(12) United States Patent
Plassky et al.

(10) Patent No.: US 7,497,029 B2
(45) Date of Patent: Mar. 3, 2009

(54) DEVICE FOR DETERMINING THE POSITION OF AN INCISION BLOCK

(75) Inventors: Norman Plassky, Erfurt (DE); Timo Neubauer, Feldkirchen (DE)

(73) Assignee: BrainLAB AG, Feldkirchen (DE)

( * ) Notice: Subject to any disclaimer, the term of this patent is extended or adjusted under 35 U.S.C. 154(b) by 737 days.

(21) Appl. No.: 11/050,421

(22) Filed: Feb. 3, 2005

(65) Prior Publication Data

US 2005/0190380 A1  Sep. 1, 2005

Related U.S. Application Data

(60) Provisional application No. 60/552,354, filed on Mar. 11, 2004.

(30) Foreign Application Priority Data

Feb. 3, 2004 (EP) .................................. 04002321

(51) Int. Cl.
*A61B 17/15* (2006.01)
*A61B 17/60* (2006.01)

(52) U.S. Cl. ..................... 33/645; 33/512; 606/102; 269/254 CS (58) Field of Classification Search .............. 33/511, 33/512, 558.3, 572, 645; 248/71, 229.11, 248/229.16, 229.21, 229.26, 231.9; 600/424; 606/62, 88, 90, 102; 269/143, 249, 254 CS, 269/3, 6, 95; 29/239, 257, 276; 403/325, 403/329
See application file for complete search history.

(56) References Cited

U.S. PATENT DOCUMENTS

| 5,213,112 | A | * | 5/1993 | Niwa et al. ................. 600/587 |
| 5,417,694 | A | * | 5/1995 | Marik et al. ................. 606/88 |
| 5,688,279 | A | * | 11/1997 | McNulty et al. ............. 606/88 |
| 5,690,638 | A | * | 11/1997 | Dance et al. ................ 606/88 |
| 5,910,143 | A | * | 6/1999 | Cripe et al. .................. 606/87 |
| 6,059,531 | A | * | 5/2000 | Tai ......................... 416/220 A |
| 6,073,360 | A | * | 6/2000 | Struble ..................... 33/783 |
| 6,551,325 | B2 | | 4/2003 | Neubauer et al. .......... 606/88 |
| 7,029,477 | B2 | * | 4/2006 | Grimm ...................... 606/88 |
| 7,111,863 | B2 | * | 9/2006 | Ward et al. ................. 280/477 |
| 7,337,515 | B2 | * | 3/2008 | Phillips et al. .............. 29/254 |
| 2002/0068942 | A1 | * | 6/2002 | Neubauer et al. .......... 606/88 |
| 2002/0107522 | A1 | | 8/2002 | Picard et al. |
| 2003/0225329 | A1 | * | 12/2003 | Rossner et al. ............ 600/424 |
| 2005/0149040 | A1 | * | 7/2005 | Haines et al. .............. 606/88 |
| 2005/0215888 | A1 | * | 9/2005 | Grimm et al. ............. 600/426 |

(Continued)

FOREIGN PATENT DOCUMENTS

EP  1 249 207  10/2002

(Continued)

*Primary Examiner*—R. A. Smith
(74) *Attorney, Agent, or Firm*—Renner, Otto, Boisselle & Sklar, LLP (57) ABSTRACT

The invention relates to a device for determining the position of a plane or recess of an instrument. The device includes a positioning element that has at least one reference marker, wherein a spatial position of the positioning element can be ascertained, and a position determining element coupled to the positioning element. The position determining element includes at least one reference element that defines a contact plane, and at least one pressing element.

31 Claims, 13 Drawing Sheets

U.S. PATENT DOCUMENTS

2006/0052792 A1* 3/2006 Boettiger et al. .............. 606/88
2006/0149287 A1* 7/2006 Lavallee ..................... 606/102
2007/0022592 A1* 2/2007 Zhou et al. ................... 29/239

FOREIGN PATENT DOCUMENTS

| | | |
|---|---|---|
| EP | 1 603 466 | 12/2005 |
| FR | 2 830 743 | 4/2003 |
| WO | 00/41635 | 7/2000 |
| WO | 2004/017842 | 3/2004 |

* cited by examiner

DEVICE FOR DETERMINING THE POSITION OF AN INCISION BLOCK

RELATED APPLICATION DATA

This application claims priority of U.S. Provisional Application No. 60/552,354 filed on Mar. 11, 2004, which is incorporated herein by reference in its entirety.

FIELD OF THE INVENTION

The present invention relates to a device for determining the position of a medical operating instrument, such as an incision block, for example, and/or the position of surfaces, such as a surface of a bone, for example. In particular, the invention relates to a device that can be used when ascertaining a spatial position or when positioning an element.

BACKGROUND OF THE INVENTION

When inserting implants, such as, for example, artificial knee, elbow, finger or hip joints, it is necessary to position the implant on the bone as precisely as possible. To this end, precise incisions must be made to the bone structures that interface with the implant.

Figure 17:
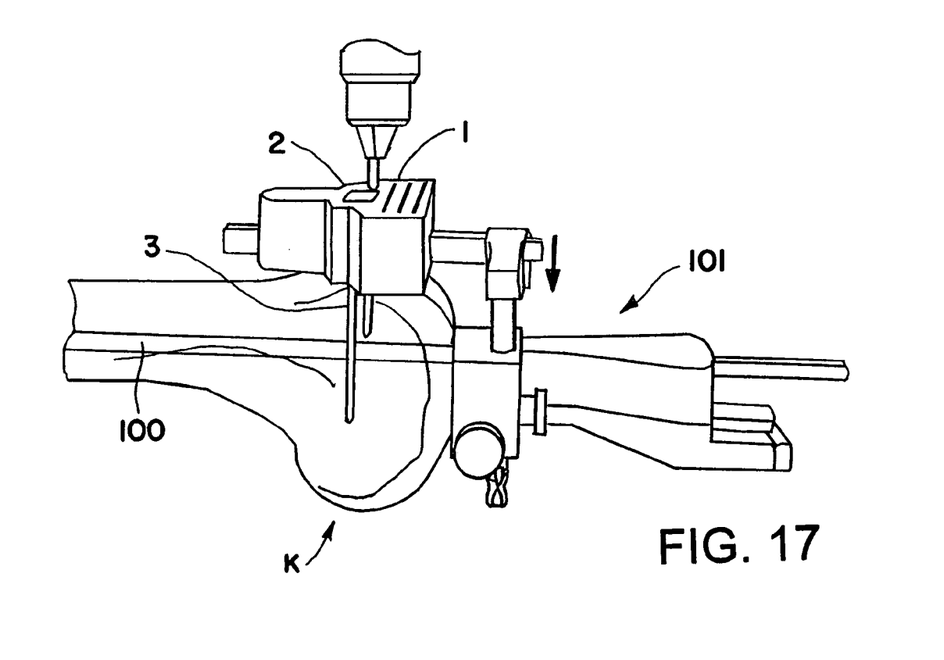
FIG. 17 illustrates an incision block being positioned on a femur bone in accordance with the prior art.

FIG. 17 schematically shows an incision block 1 being positioned on a femur bone K in accordance with the prior art. To this end, a guiding rod 100 is inserted into the bone K, wherein a positioning mechanism 101 for positioning and holding the incision block 1 in a desired position is provided at the outer end of the guiding rod 100. Once the incision block 1 has been moved to the desired position, the block 1 can be fixed to the bone using positioning pins 3, such as screws, nails and/or pins, for example, which can be inserted through holes 2 provided in the incision block 1 and into the bone K. After the incision block 1 has been successfully fixed to the bone K, a first incision plane S0, preferably as perpendicular as possible to the mechanical axis of the bone or slightly angled with respect to the mechanical axis of the bone, can be formed by means of an incision tool 4, as shown schematically in FIGS. 14A and 14B. In order to position the corresponding knee implant component on the bone K, additional incisions are made in additional incision planes S1 to S4 running obliquely to or angled with respect to the incision plane S0, as shown in FIG. 15. To this end, a second incision block 10 is placed onto the bone K at the first incision plane S0 and positioned by means of a suitable mechanism. The incision tool 4, which is guided by obliquely or laterally running slits of the second incision block 10, is used to make the additional lateral incisions to the bone.

Figure 16:
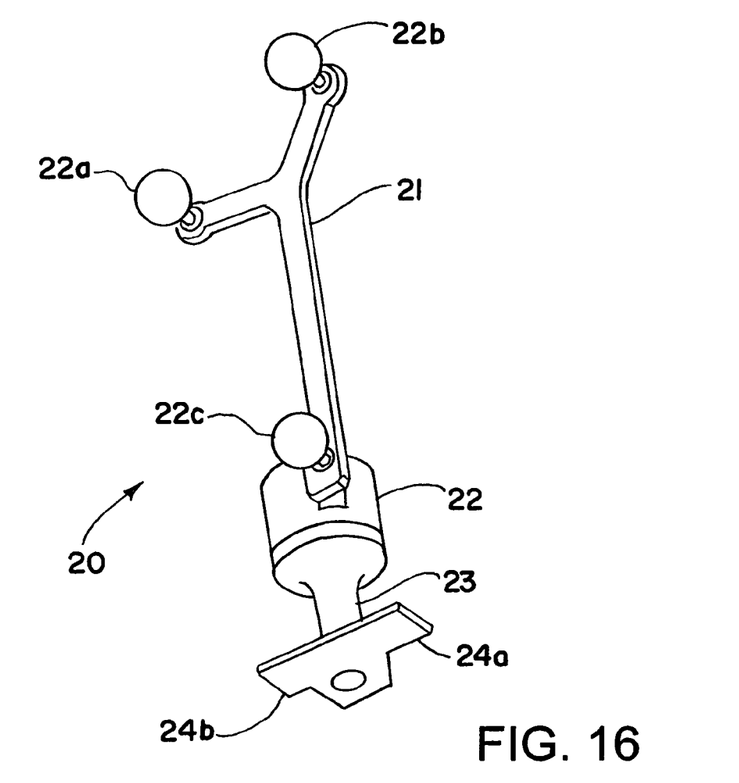
FIG. 16 illustrates a prior art device for positioning an incision block.

A device 20 for determining the position of an incision block as shown in FIG. 16 is known from European Patent No. EP 1 190 676 A1 and corresponding U.S. Pat. No. 6,551,325 belonging to the Applicant, the disclosure of which is hereby incorporated by reference. The device includes a reference star 21 having a plurality of arms 21a, 21b, 21c extending therefrom. Spherical markers 22a, 22b, 22c, each having a reflective surface, are coupled to the arms, wherein two infrared cameras (not shown) detect infrared light reflected on the spherical markers 22a, 22b, 22c. Based on the incident and reflected infrared light, the cameras can ascertain the three-dimensional spatial position of the reference star 21.

Figure 13:
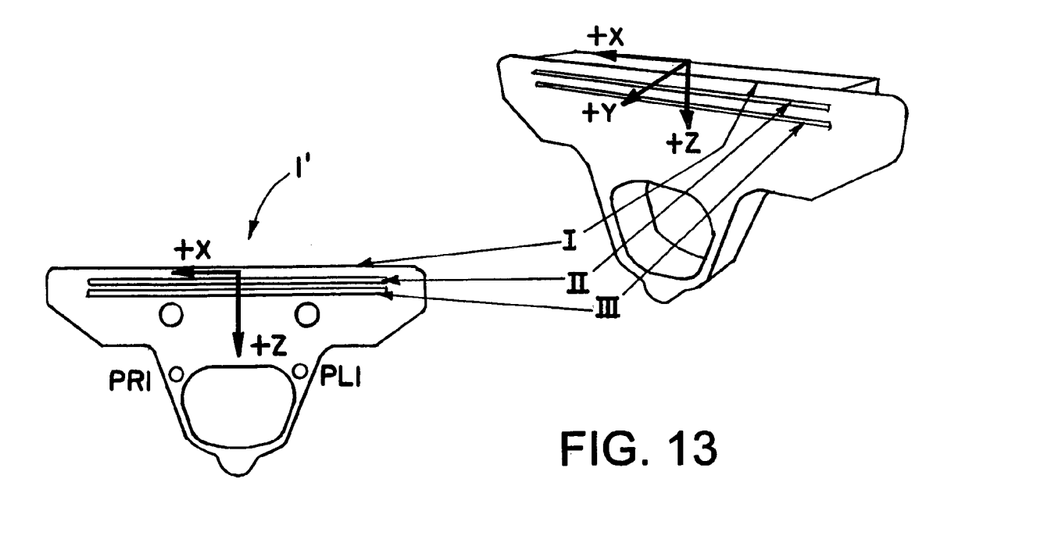
FIG. 13 illustrates two views of a femoral incision block.

The reference star 21 is fixedly connected to a base body 22, to which a rotatable element 23 is attached. Two plates 24a, 24b of different thicknesses are arranged on the outer end of the rotatable element 23 and can be inserted into a guiding slit, such as the guiding slit 1a of the tibial incision block 1 shown in FIGS. 12A to 12E. Alternatively, the plates 24a, 24b can be inserted or into one of the guiding slits II, III of the femoral incision block 1' shown in FIG. 13.

Figure 14A:
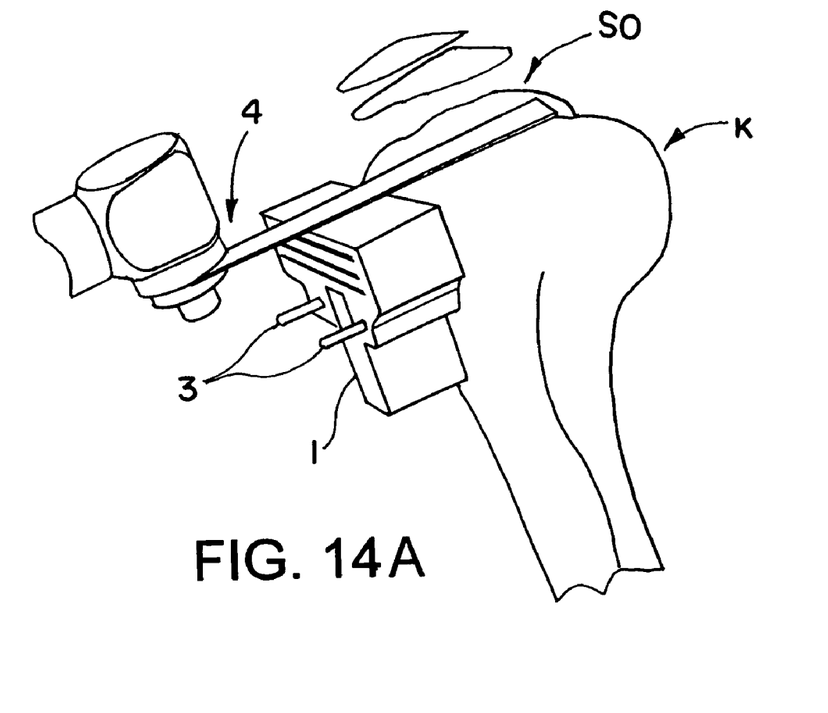
FIGS. 14A-14B illustrate a bone being cut using a positioned incision block.
Figure 14B:
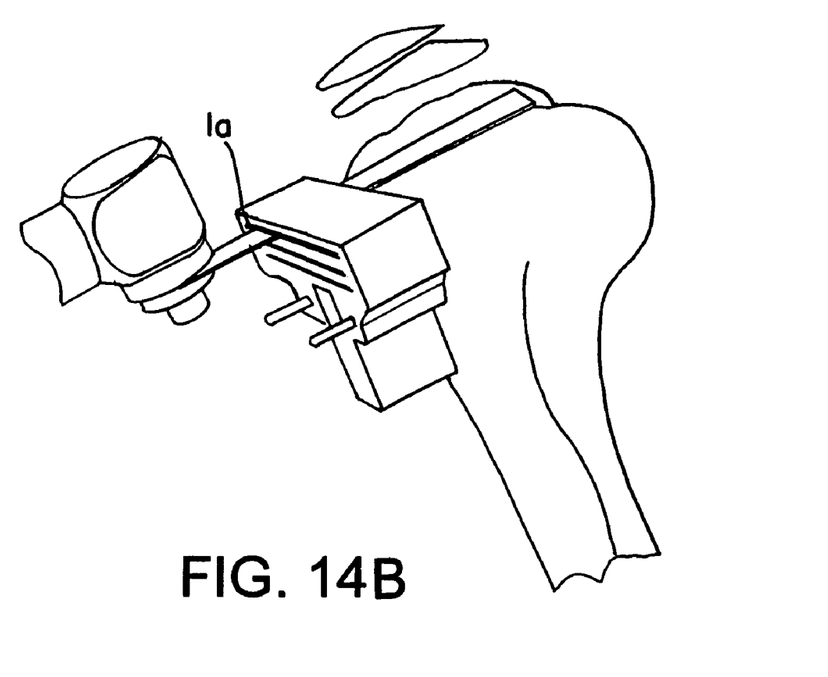
Figure 15:
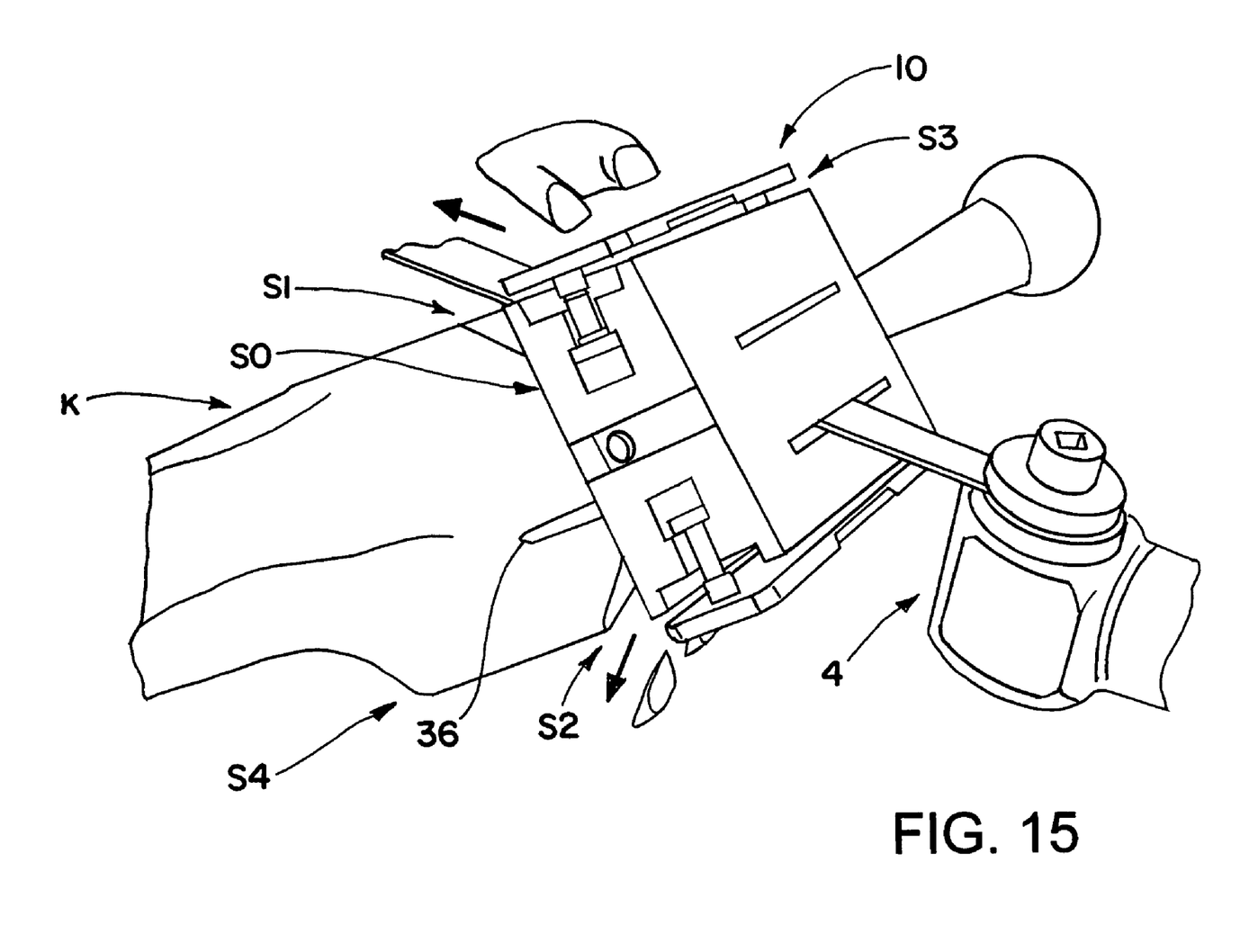
FIG. 15 illustrates incision planes S1 to S4 being cut using a second incision block.

In order to make the incision shown in FIG. 14, the incision block 1 is navigated to the desired point on the bone K and then is fixed to the bone K using fixing elements 3. An incision is made in the desired incision plane using the incision tool 4, as shown in FIG. 14B. A second incision block 10 then is placed on the incision plane S0 formed by the first incision, as shown schematically in FIG. 15, and incisions are made in the planes S1 through S4 using the guiding slits provided in the second incision block 10. Once the incisions are completed, an artificial joint can be placed on the bone and, provided the incision planes S0-S4 are correctly positioned, the artificial joint also will be correctly positioned.

Repeated use of the positioning device 20 described above, however, can lead to attrition in the area of the plates 24a and 24b shown in FIG. 16. Additionally, repeated use of the incision tool 4 may enlarge the guiding slits 1a, I,II,III. Plate attrition and/or enlargement of the slits can result in excessive clearance between the plates 24a, 24b and the walls of the slits 1a, I, II, III, thus allowing the reference star 21 to move with respect to the incision block. Movement of the reference star with respect to incision block can result in misalignment of the incision block 1, 1' and, therefore, misalignment of the incision planes S0-S4.

SUMMARY OF THE INVENTION

The present invention provides a coupling means between a reference star and incision block slits that minimizes the effects of plate attrition and/or slit wear, thereby increasing the accuracy of the incision planes.

According to one aspect of the invention, the invention relates to a device for determining the position of a plane or recess of an instrument. The device includes positioning element that has at least one reference marker, wherein a spatial position of the positioning element can be ascertained, and a position determining element coupled to the positioning element. The position determining element includes at least one reference element that defines a contact plane, and at least one pressing element.

Another aspect of the invention relates to a device for determining the position of a plane or recess of an instrument. The device includes a positioning element, a connector coupled to the positioning element, and a biasing element. The connector includes a substantially flat plate that defines a reference plane, and the biasing element is operatively coupled to the connector, wherein the biasing element provides a force having at least one component that is substantially perpendicular to the reference plane.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

These and further features of the present invention will be apparent with reference to the following description and drawings, wherein.

DETAILED DESCRIPTION

The present invention relates to a device that can be repeatedly fixed to an instrument without being affected by wear of the instrument and/or of the device itself. As used herein, an instrument refers to any object that includes a surface to be navigated, including, but not limited to, incision blocks used for making incisions in bones.

A device in accordance with the present invention includes a positioning element and a position determining element. The positioning element, for example, includes a reference star whose spatial position can be detected by a navigation system. Navigation systems are well known in the art and will not be discussed herein. Further information regarding medical navigation systems can be found in U.S. Patent Publication No. 2003/0225329, which is hereby incorporated by reference.

The reference star includes at least one reference point or marker, which can be active and/or passive elements that emit and/or reflect suitable signals. The signals can be detected by corresponding recording apparatus, such as cameras, for example, and used to determine the spatial position of the positioning element and any instrument coupled thereto.

The position determining element, which is fixedly connected to the positioning element, interfaces with the instrument. In accordance with the invention, the position determining element includes a reference element, such as a reference plate, for example. One surface of the reference element, which serves as a reference plane, can interface with the instrument to be navigated. In accordance with the invention, at least one pressing element or tensing element is provided with respect to the reference element. The pressing or tensing element enables the reference plane of the reference element to be pressed against a surface of the instrument to be navigated.

For example, prior to cutting a bone with the aid of an incision block, the guiding surface or "slit" of the incision block first is positioned. The reference element of the position determining element is inserted into the slit of the incision block. Additionally, the pressing or tensing element provides a force to the reference element that tends to keep the reference plane of the reference element against a wall of the slit. Thus, the reference plane of the reference element is firmly against the wall of the slit and, therefore, the position of the slit can be precisely determined.

The at least one pressing element in accordance with the invention can be formed such that one or more pressing elements or pressing plates can be biased with respect to the reference element by a force generated by a spring or a tensing element, for example. The reference element in combination with the at least one biased pressing element can be tightly tensed or pinched in a recess of an instrument, irrespective of whether the recess exhibits a precisely predetermined thickness or deviates slightly from a predetermined thickness. As used herein, a recess refers to any surface to be navigated, such as an opening, plane or slit in an instrument. It should be appreciated, however, that a surface other than the recess may be navigated, wherein the recess is used to navigate the other surface, provided the geometric relationship between the recess and the other surface is known. In accordance with the invention, the pressing element biased by a force thus can prevent the reference element and, therefore, the positioning element from being in an imprecisely defined positional relationship with respect to the instrument connected to the positioning element.

In one embodiment, the position determining element or a part thereof, e.g., the reference element and/or the pressing element, can be rotated about an axis relative to the positioning element. The axis can be parallel to a normal of the reference plane of the reference element. In another embodiment, the position determining element, the reference plane and/or the axis can be shifted, wherein the reference element is formed such that the contact surface on the reference element, which forms the reference plane, only can be shifted within the reference plane. In yet another embodiment, the positioning element includes a reference star having three passive markers coupled thereto. The reference star can be used to navigate the reference plane formed by the position determining element.

The reference element and/or pressing element can include at least one plate that can be inserted into an instrument. Alternatively, a number of individual plate elements, preferably lying in one plane, also can be used as the reference and/or pressing element. Additionally, the pressing element and/or the pressing plate can be moved in a direction perpendicular to the reference plane formed by the reference element. A part of the pressing element, e.g., the pressing plate, can be formed such that it can be inserted into an opening in the reference element, wherein the pressing element exhibits approximately the same thickness as a thickness of the plate used for the reference element. In such a configuration, the reference element and the pressing element together can be inserted into the recess of an instrument.

A biasing element, such as a spring, charges the pressing element with a force that acts beyond and preferably perpendicular to the plane defined by the reference element. As the reference element is inserted into a recess together with the pressing element and/or the pressing plate, the biasing element tends to move the pressing element away from the reference element until the pressing element (and/or the pressing plate) and the reference element firmly contact opposing lateral surfaces of the recess. The firm contact establishes a fixed and defined connection between the positioning element and the instrument.

The biasing element can be formed by one or more springs, such as spiral (e.g., a coil spring) or torsion springs, wherein the spring is provided between the reference element and the pressing element. In order to move the pressing element with respect to the reference element, a force is applied to the pressing element and, in the case of a coil spring, the spring is compressed. The spring generates a restoring force that tends to move the pressing element away from the reference element. Depending on the relative separation between the pressing element (and/or pressing plate) and the reference element, a non-positive or positive connection to the recess in the instrument is provided.

The biasing element can be formed both as a pressure spring, a tension spring or a leaf spring. In one embodiment, the biasing element provides a force such that the pressing element and/or pressing plate is moved away from the reference element. In another embodiment, the biasing element provides a force such that the pressing element and/or pressing plate is moved towards the reference element.

The biasing element can be provided on the device in accordance with the invention, such that a rotational movement of a freely rotatable positioning element can be inhibited by the force generated by the biasing element, and the positioning element can be fixed or arrested in a fixed position.

In accordance with another embodiment, the invention relates to a system for positioning an incision block, including a device as described above and an incision block. The incision block includes at least one slit that can be used as a guiding slit, wherein the position determining element and, in particular, the reference element (which is fixedly connected to the positioning element) can be inserted. The device described also can be used to navigate any instrument that includes a surface to be navigated, such as a recess, wherein the device directly or indirectly interfaces with the surface to be navigated.

Accordingly, the present invention enables a positioning element to be coupled to an instrument, thereby facilitating navigation of a surface of the instrument. Moreover, the coupling point of the instrument can exhibit different thicknesses without affecting the accuracy of the device. Furthermore, the invention can ensure that a reference plane formed by a reference element can be navigated, provided the geometry between the positioning element and the reference element (or a contact surface of the device serving as a reference plane) is defined. Additionally, the pressing element used to couple the device to the instrument can be used to securely fix the device to recesses having various thicknesses, such that the device in accordance with the invention can be implemented in software as a pre-calibrated device. It also is possible for a contact surface to serve as a reference plane and thereby be used to verify the position of a surface, such as, for example, an incision on a bone.

Referring now to FIGS. 1 and 2A-2C, a device 20 in accordance with an embodiment of the invention is illustrated. The device 20 includes a reference star 21 having three arms 21a, 21b, 21c. Three markers 22a, 22b and 22c, each having a reflective spherical surface, are fixed to the arms 21a, 21b, 21c. The reference star 21 is connected to a reference star holder 15 via a connecting element 11, which can be formed as a clamp or a socket. The connecting element 11 enables a rotational movement of the reference star 21 about an axis 25 of the device 20.

Figure 1:
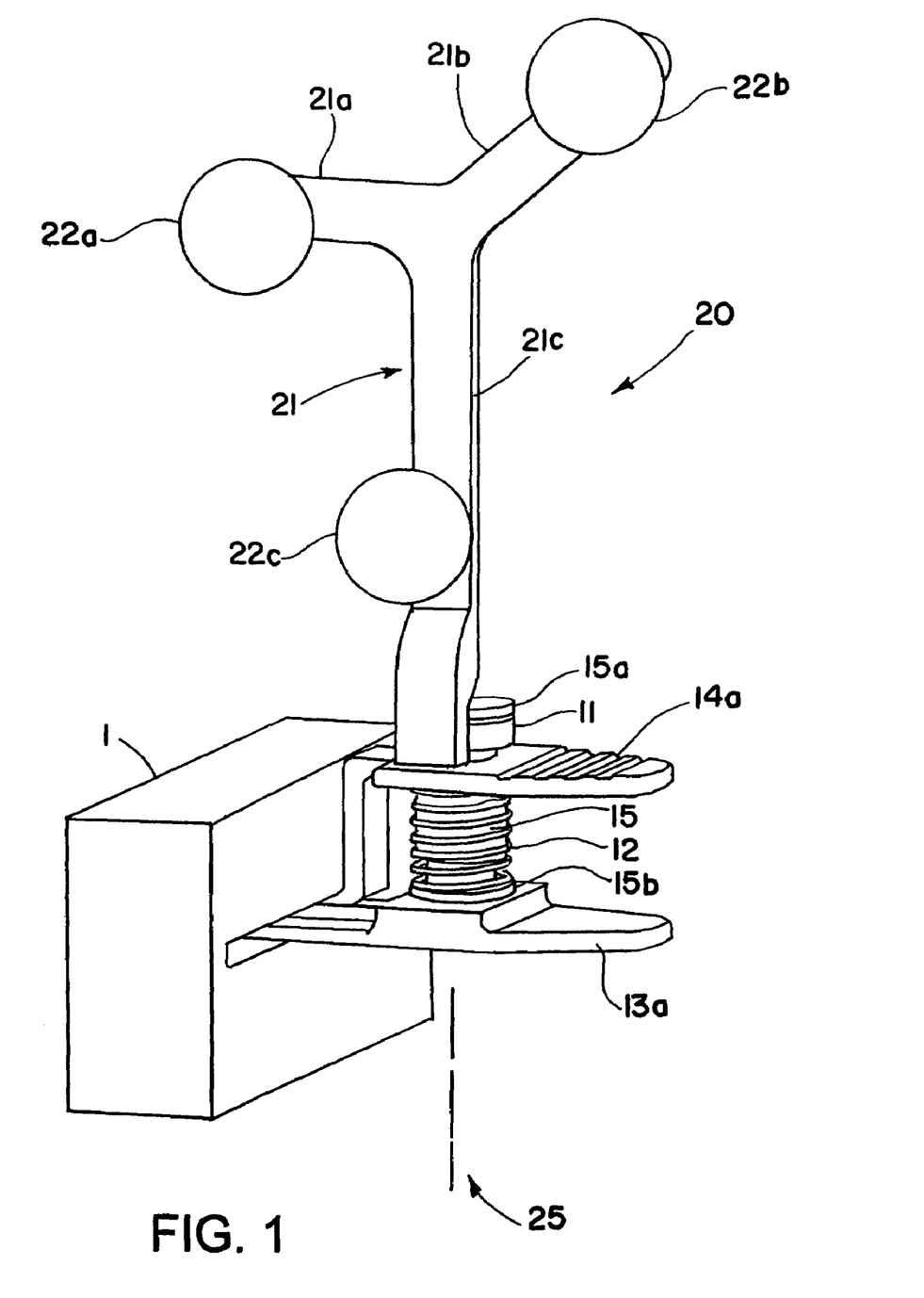
FIG. 1 illustrates an isometric view of a reference star coupled to a device in accordance with an embodiment of the present invention, wherein the device is shown coupled to an incision block.
Figure 2A:
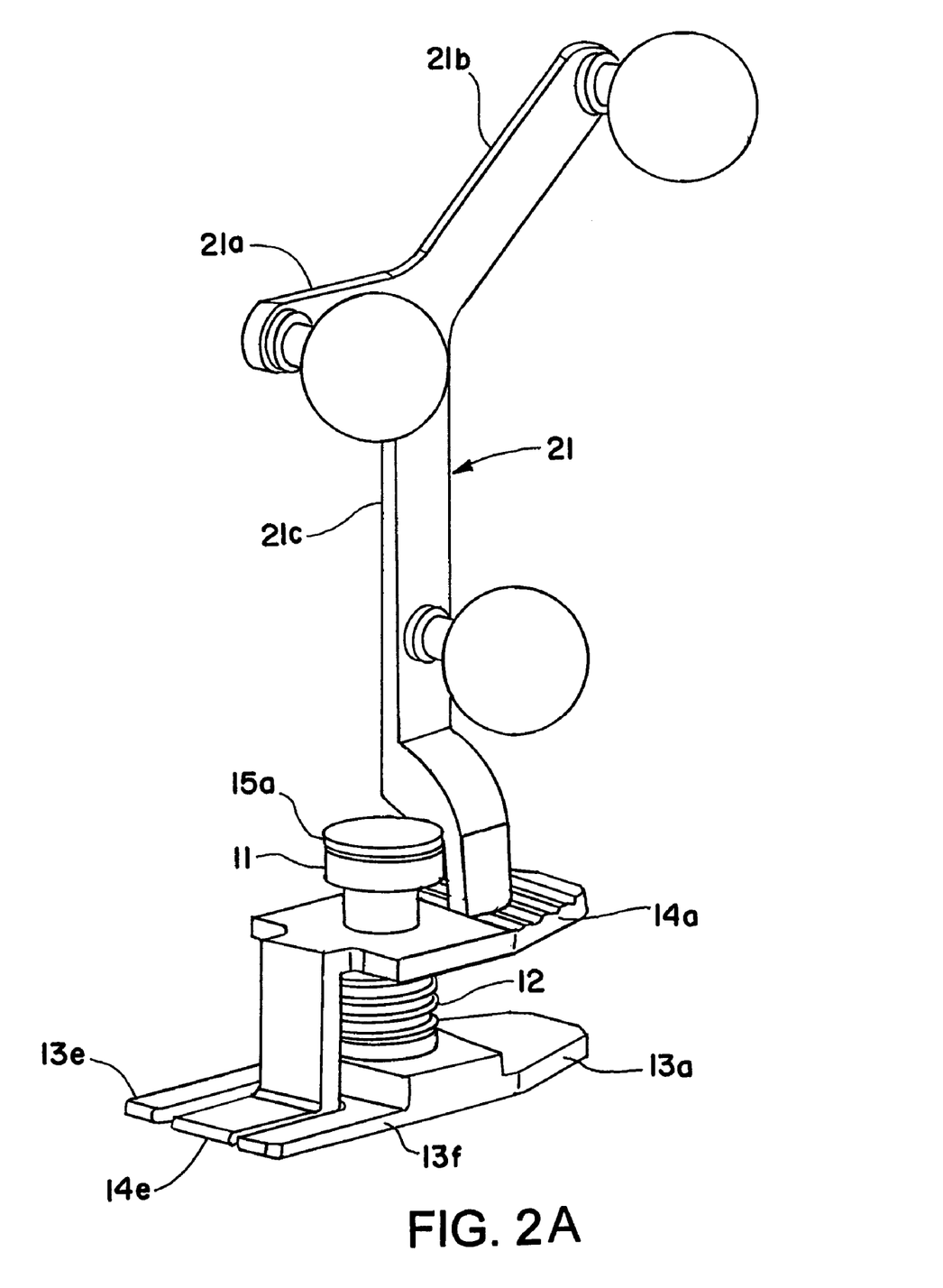
FIG. 2A illustrates an isometric view of the device of FIG. 1 without being coupled to the incision block.
Figure 2B:
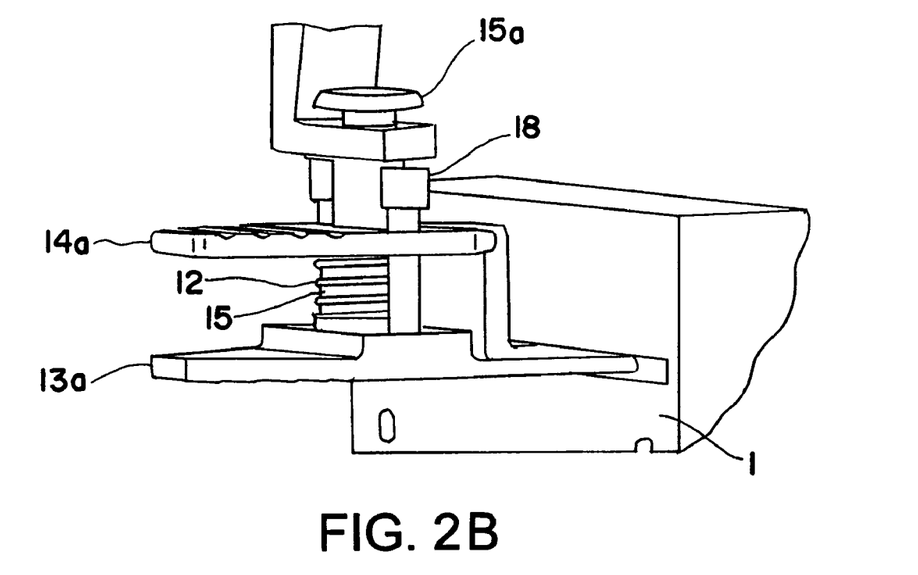
FIG. 2B is an isometric view of a coupling mechanism of the device in accordance with an embodiment of the present invention, wherein the coupling mechanism is shown coupled to an incision block.

The reference star holder 15 includes disc-shape closing elements 15a and 15b at each of its upper side and lower side. The upper closing element 15a shown in FIG. 1 prevents the connecting element 11 from detaching from the reference star holder 15. The reference star holder 15 protrudes through an opening of the pressing element 14a and is connected on its lower side to the reference element 13a via the lower closing element 15b. The lower surface of the reference element 13a serves as a reference plane for the device 20. A spring 12 is supported on the upper side of the lower closing element 15b and presses against the upper side of the pressing element 14a, thus pressing the pressing element 14a away from the reference element 13a. The pressing element 14a is formed in steps and includes a pressing plate 14e, which can be shifted between two reference plates 13e and 13f of the reference element 13a, as shown in FIG. 2A. Pins 26 (FIGS. 2B and 2C) guide the pressing element 14a as it is moved with respect to the reference element 13a.

In use, a force is applied between the pressing element 14a and the reference element 13a, tending to urge the pressing element towards the reference element, thereby compressing the spring 12. The pressing plate 14e, which is coupled to the pressing element 14a, moves along with the pressing element. When the pressing plate 14e and the reference plates 13e, 13f are substantially parallel to one another, they may be inserted into a recess of an instrument, e.g., the slit of the incision block 1, such that once the force is removed, the pressing element 14a is shifted upwards relative to the reference element 13a by the stored energy in the spring 12, thereby moving the pressing plate 14e upward with respect to the reference plates 13e, 13f. The pressing plate 14e and reference plates 13e, 13f each contact opposing lateral surfaces of the recess, thereby fixedly connecting the device 20 to the instrument. Moreover, the positional relationship between the reference star 21 and the reference plane formed by the lower side of the reference element 13a remains constant, such that the surface of the recess in the instrument contacting the reference plane can be navigated by means of the reference star 21. Furthermore, the reference star 21, due to the spring force acting on the lower closing element 14b, is arrested and can no longer be rotated.

Figure 2C:
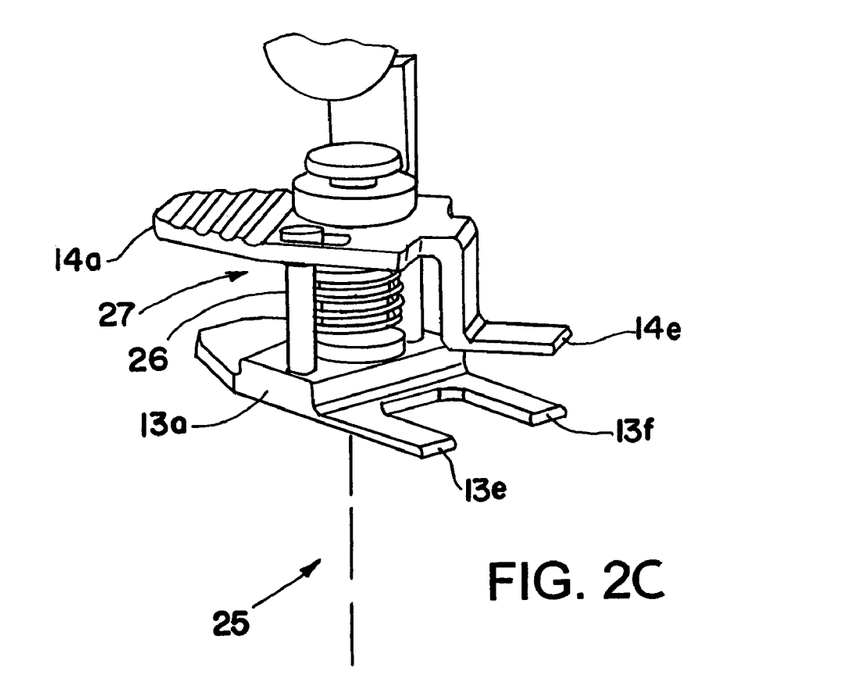
FIG. 2C is an isometric view of the coupling mechanism of the device as a pressing element is moved with respect to a reference element.

With further reference to FIG. 2C, the pressing element 14a is shown moved away from the reference element 13a (and thus the pressing plate 14e moved away from the reference plates 13e, 13f). This is advantageous, for example, in that it allows the device 20 to easily be cleaned. The pressing element 14a can be rotated about the axis 25 by applying a force to the pressing element with respect to the reference element. Stabilizing pins 26 are fixed to the reference element 13a and extend upward substantially perpendicular to the reference element. Slots 27 in the pressing element 14a interface with the pins, whereby the pins guide the pressing element as it is moved with respect to the reference element. Moreover, the slots 27 are non-circular in shape, e.g., oval slots, thereby permitting the pressing element to be rotated about the axis 25, while remaining coupled to the pins.

Accordingly, the above device in accordance with an embodiment of the invention can be used to navigate a surface of an instrument. Moreover, the device can be firmly attached to the instrument, without being affected or only minimally affected by wear of the navigated surface and/or by attrition of the device itself. Furthermore, the device can be manipulated so as to facilitate cleaning of the device.

FIGS. 3-11 illustrate alternative embodiments of the present invention. It should be understood that the following embodiments incorporate many of the components and features of the above described embodiment and, for sake of brevity, only differences from the above described embodiment will be discussed.

Figure 3:
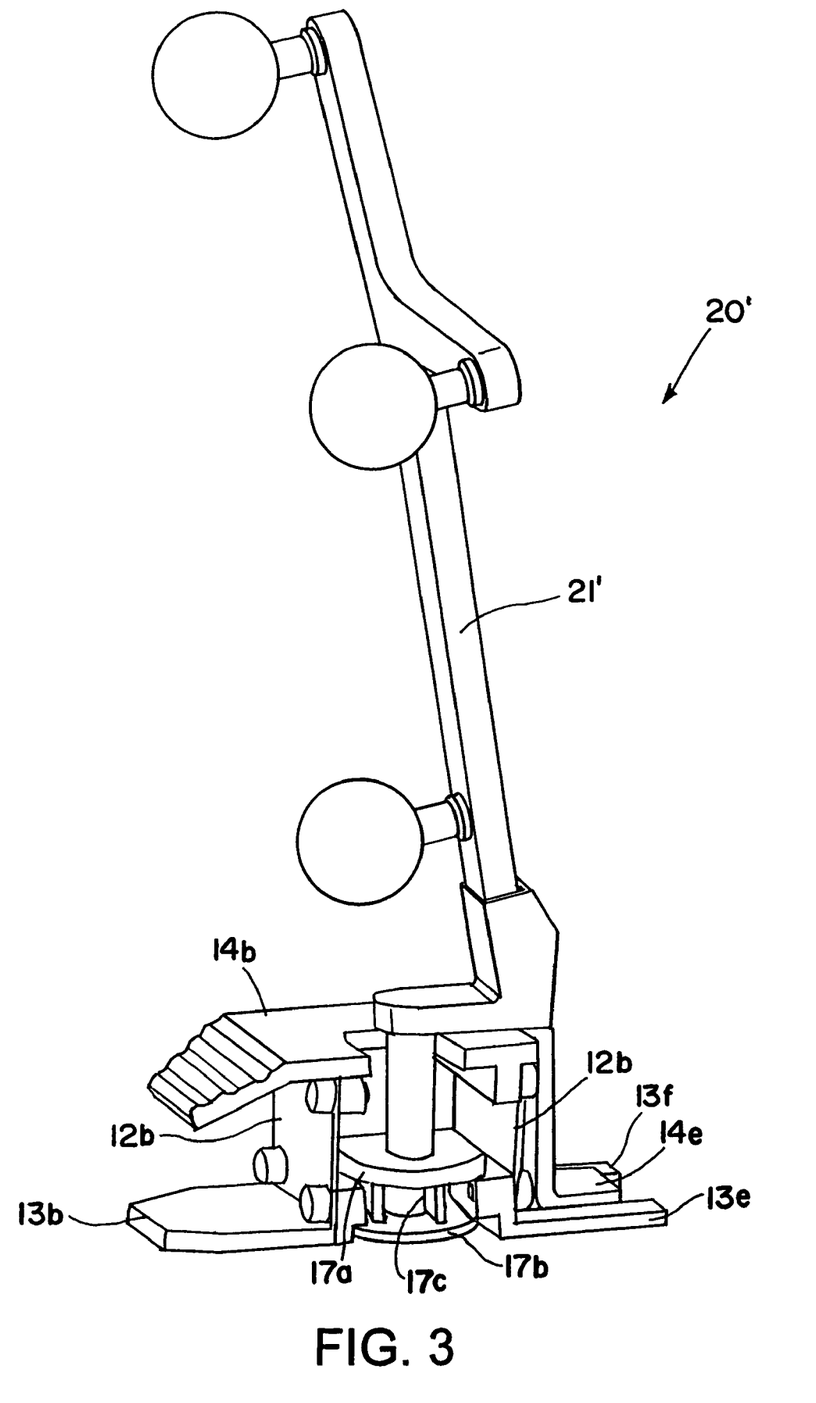
FIG. 3 is an isometric view of the device in accordance with another embodiment of the present invention.
Figure 4:
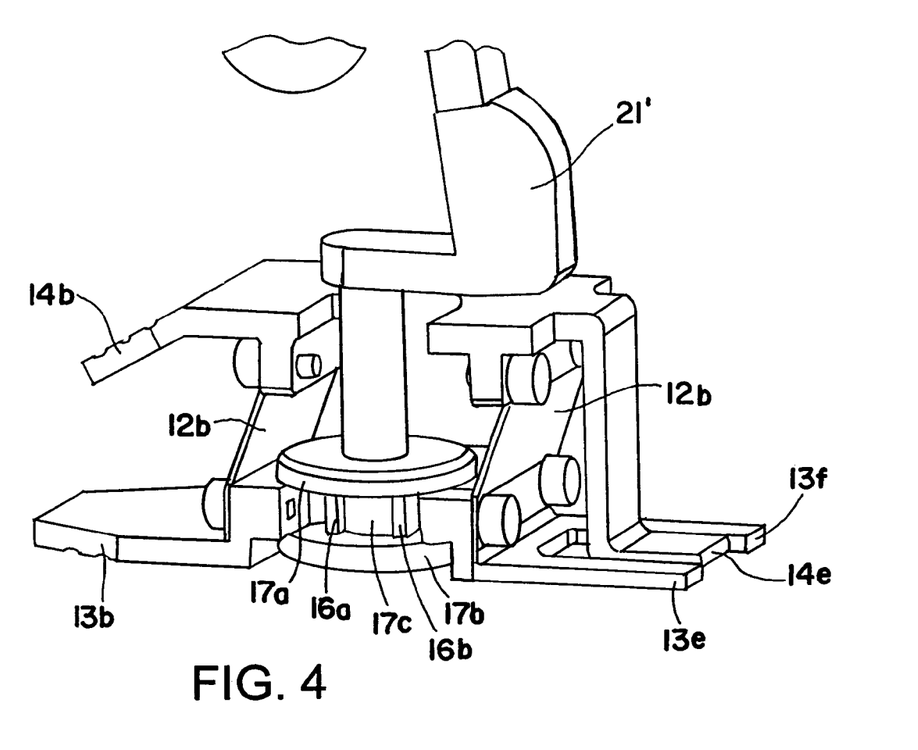
FIG. 4 is a side perspective isometric view of the coupling mechanism of the device of FIG. 3.
Figure 5:
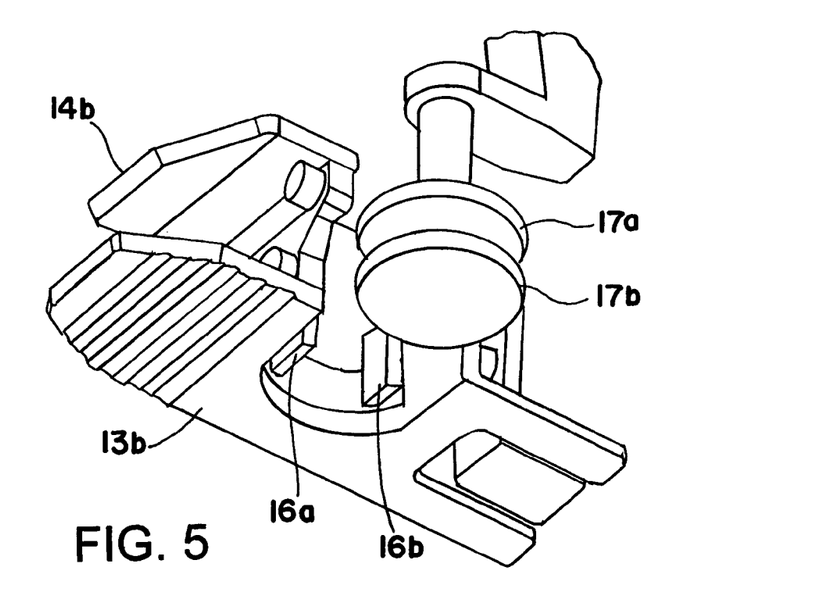
FIG. 5 is a bottom perspective isometric view of the coupling mechanism of the device of FIG. 3.

Moving now to FIGS. 3 through 5, a second embodiment of the device 20' is illustrated. The device 20' includes a reference star 21' having two rings 17a, 17b separated from each other by a distancing piece 17c. The distancing piece 17c of the reference star 21' can be connected to a reference element 13b via two locking elements 16a, 16b, thereby forming a clamping point.

The reference element 13b is connected to a pressing element 14b via two leaf springs 12b running substantially perpendicular with respect to the reference element 13b. It should be appreciated that the orientation of the springs is not critical, and other angles (e.g., not perpendicular) may be employed without departing from the scope of the invention. The pressing element 14b can be moved out of the initial position shown in FIG. 3 by applying a force to the pressing element 14b. The force laterally shifts the leaf springs 12b and causes a pressing plate 14e, which is connected to the pressing element 14b, to move between a pair of reference plates 13e and 13f of the reference element 13b, as shown in FIG. 4. If the reference plates 13e and 13f are inserted into a recess of an instrument together with the pressing plate 14e and the force is removed, then the leaf springs 12b generate a restoring force on the pressing element 14b relative to the reference element 13b. A component of the restoring force also acts perpendicularly to the lower surface of the reference element 13b, which serves as a reference plane.

As the force is applied to the pressing element 14b, the device 20' can be moved in the recess. Removing the force, however, causes the leaf springs 12b to exert the restoring force, which tends to raise the pressing element 14b with respect to the reference element 13b and, therefore, raises the pressing plate 14e with respect to the reference plates 13e, 13f. As the pressing plate 14e is raised, it comes in contact with an upper lateral surface of the recess, while the reference plates 13e, 13f, which form the reference plane, come in contact with a lower lateral surface of the recess. Provided the leaf springs do not fully return to their relaxed position (e.g., not compressed or tensed), the reference plane and, therefore, the reference star 21' are in a known positional relationship with respect to the recess of the instrument.

Figure 6:
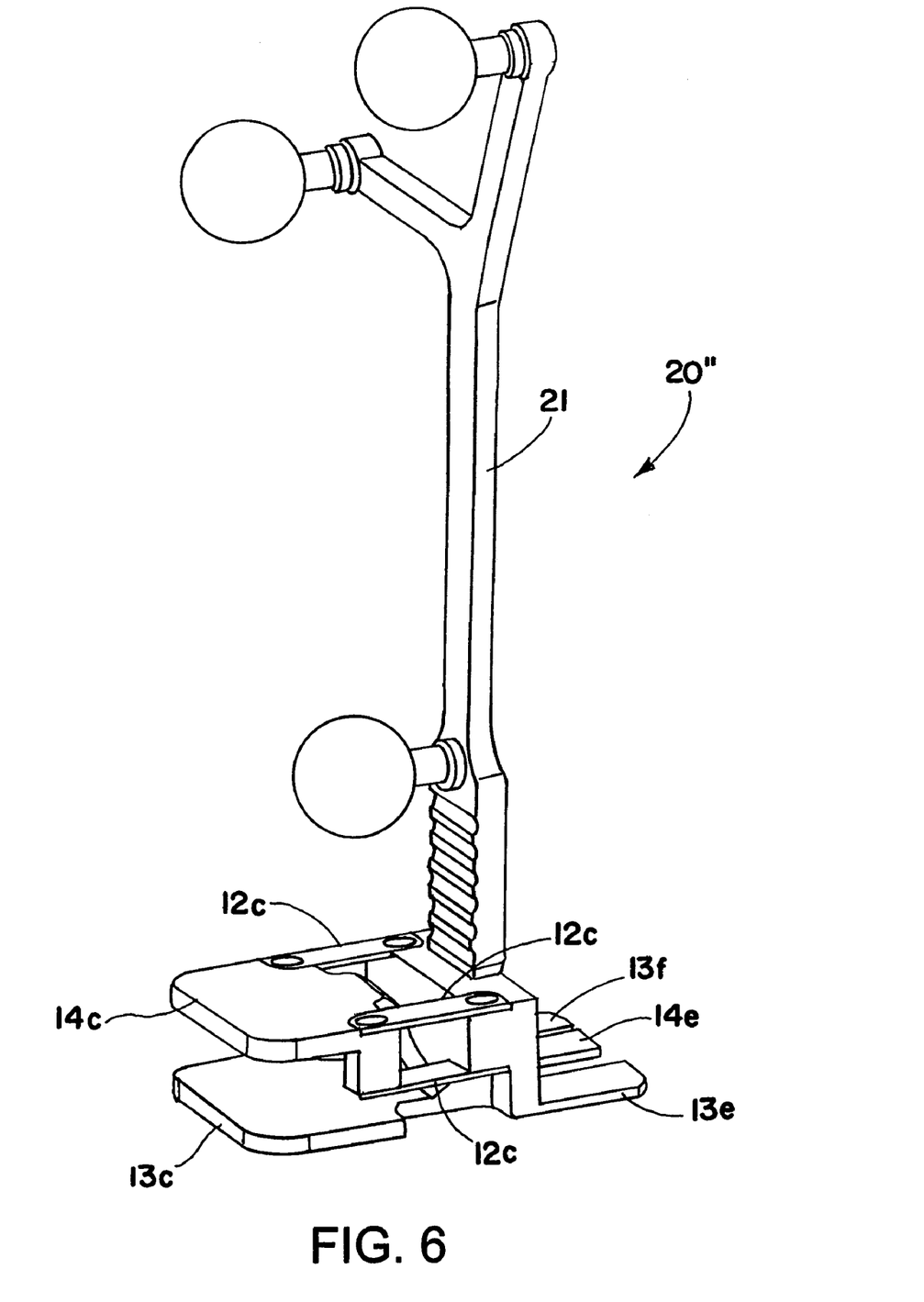
FIG. 6 is an isometric view of the device in accordance with another embodiment of the present invention.
Figure 7:
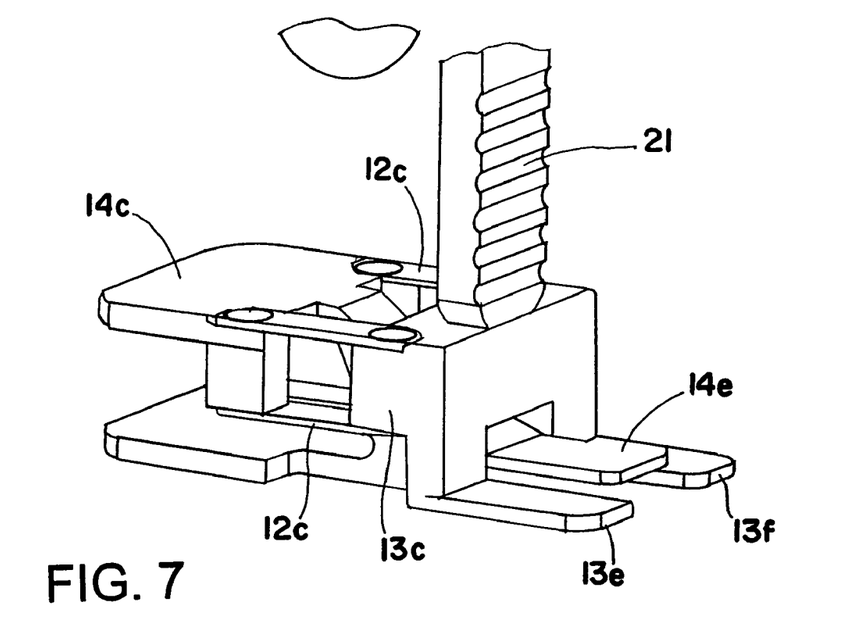
FIG. 7 is a side perspective isometric view of the coupling mechanism of the device of FIG. 6.
Figure 8:
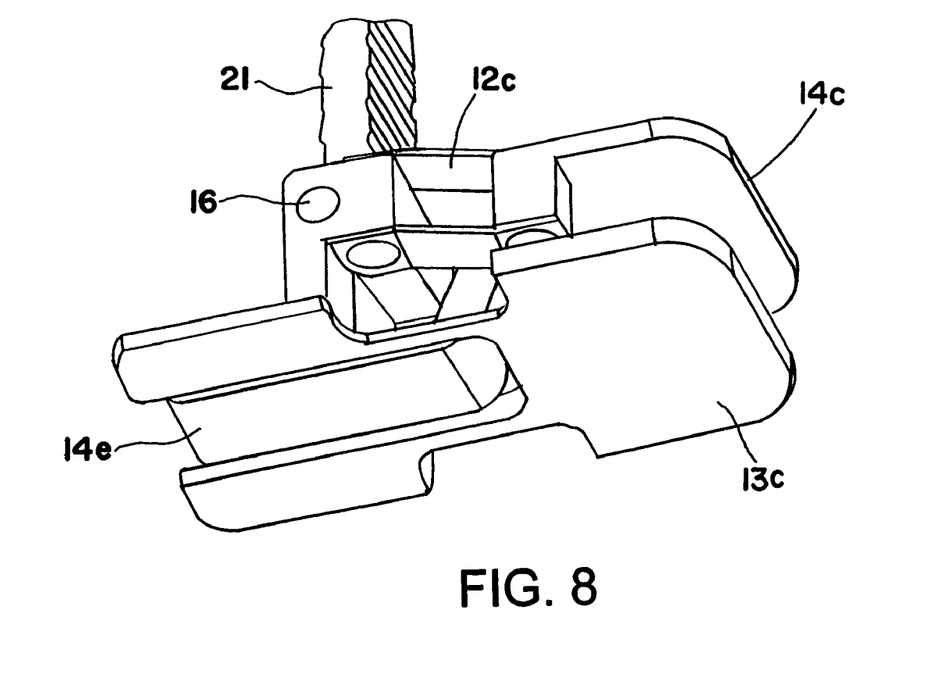
FIG. 8 is a bottom perspective isometric view of the coupling mechanism of the device of FIG. 6.

Moving now to FIGS. 6 through 8, a third embodiment of the device 20'' in accordance with the invention is shown. The device 20'' includes a pressing element 14c connected to a reference element 13c via leaf springs 12c. The leaf springs 12c run substantially horizontal or parallel to a lower surface of the reference element 13c, and can generate a force that acts on a pressing plate 14e. As was noted above, the orientation of the springs with respect to the reference element is not germane to the invention, and other angles may be employed without departing from the scope of the invention. A reference star 21 can be coupled and locked to the reference element 13c by means of a ball-thrust pin 16, which can be inserted into the reference element 13c. The reference element 13c includes two plates 13e, 13f, which form a reference plane of the reference element. The pressing element 14c is formed in steps and includes the pressing plate 14e, which can be shifted or moved between the two reference plates 13e and 13f by applying a force to the pressing element 14c.

For example, applying a force to the pressing element 14c relative to the reference element 13c will result in movement of the pressing element 14c, thereby flexing the leaf springs 12c, which tend to oppose the applied force. Furthermore, movement of the pressing element causes the pressing plate 14e to move with respect to the reference plates 13e, 13f. Positioning the pressing plate 14e substantially parallel to the reference plates 13e, 13f allows the pressing and reference plates to be inserted into a recess of an instrument. Once the force is removed from the pressing element 14c, the springs 12c apply a restoring force to the pressing element, thereby moving the pressing element 14c and the pressing plate 14e. As the pressing plate 14e moves beyond the plane formed by the reference plates 13e and 13f, a top portion of the pressing plate 14e and bottom portions of the reference plates 13e, 13f contact opposing lateral surfaces of the recess. The contact of the plates with the opposing lateral surfaces of the recess fixedly connects the reference star 21 to the instrument in a defined positional relationship. Moreover, the lateral surface contacting the reference plates 13e, 13f now can be navigated using the reference star 21.

Figure 9:
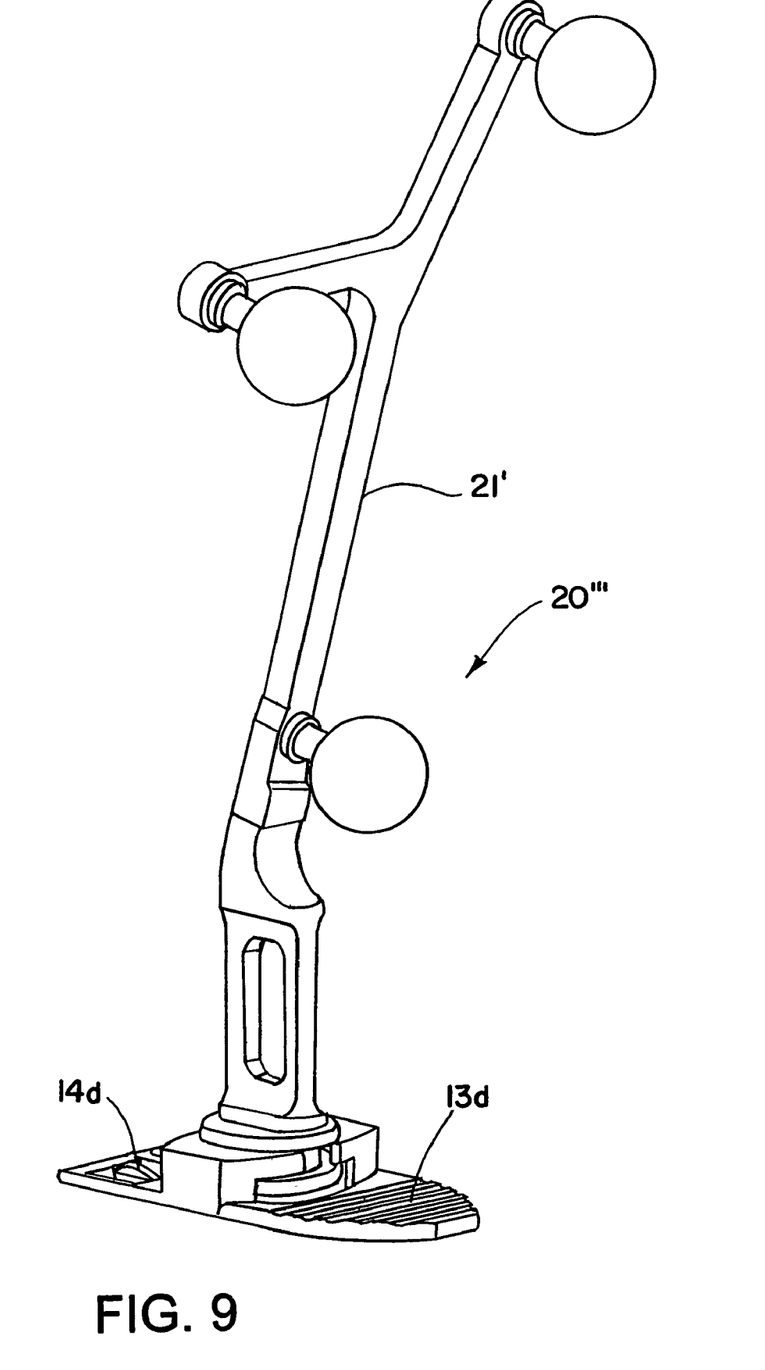
FIG. 9 is an isometric view of the device in accordance with another embodiment of the present invention.
Figure 10:
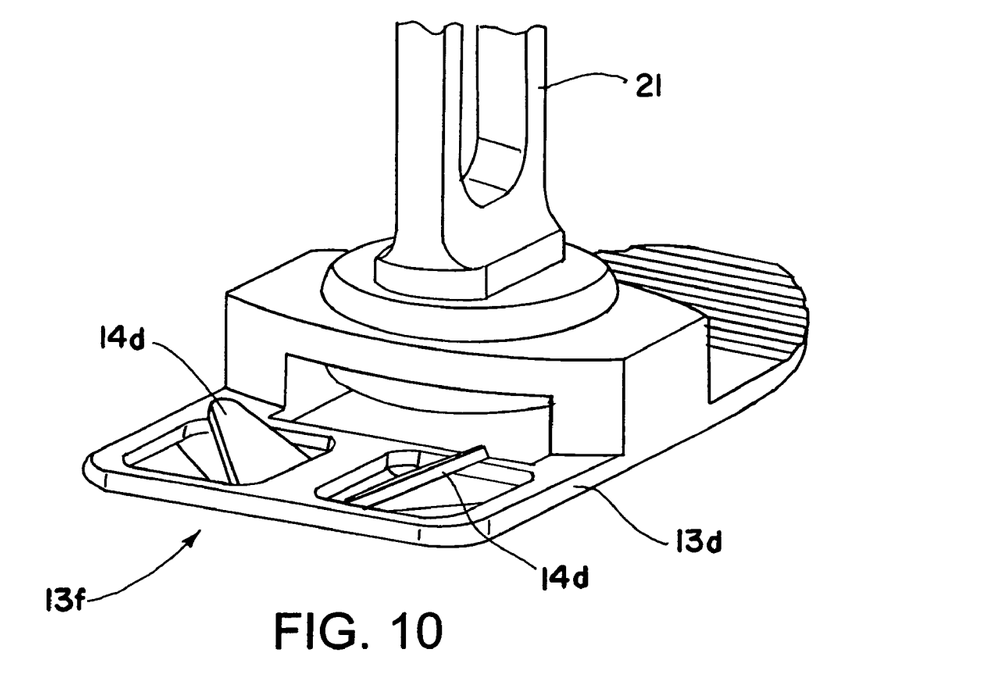
FIG. 10 is a side perspective isometric view of the coupling mechanism of the device of FIG. 9.
Figure 11:
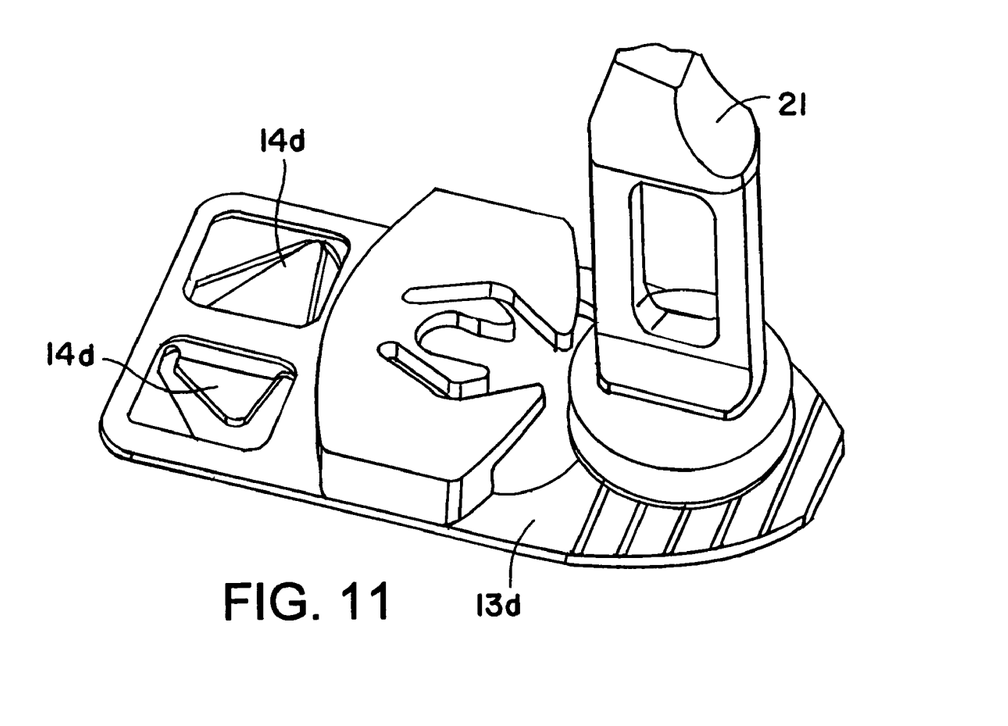
FIG. 11 is a top perspective isometric view of the coupling mechanism of the device of FIG. 9.
Figure 12A:
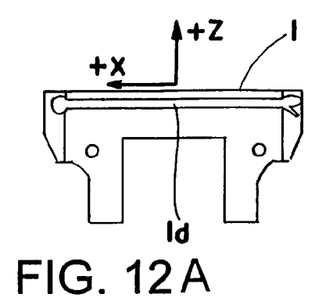
FIGS. 12A-12E illustrate various views of a tibial incision block.
Figure 12B:
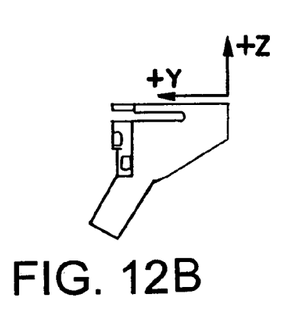
Figure 12C:
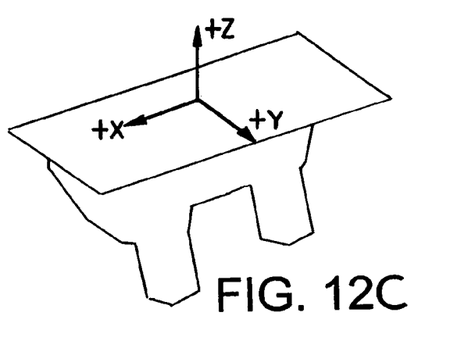
Figure 12D:
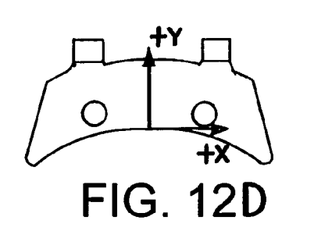
Figure 12E:
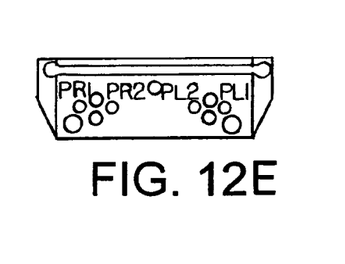

Moving now to FIGS. 9 through 11, a fourth embodiment of the device 20''' in accordance with the invention is shown. The device 20''' includes a reference star 21', which can be locked to a reference element 13d in a manner similar to that shown with respect to the embodiment of FIGS. 3-5. Unlike the preceding embodiments, however, a pressing element biased by a separate spring is not provided.

A bottom surface 13f of the reference element 13d forms a reference plane of the reference element, and elastic or spring elements 14d protrude beyond a top surface of the reference element 13d. The elastic elements 14d are chamfered along an insertion direction, thereby facilitating insertion of the reference element 13d and the elastic element 14d into a recess of an instrument. As the reference element and the elastic elements are inserted into a recess of an instrument, the elastic elements deform, thereby creating an interference fit. The elastic elements 14d apply a force against one surface of the recess, thereby pressing the bottom surface of the reference element 13d against an opposing surface of the recess. The interference fit fixedly connects the reference star 21' to the instrument in a defined positional relationship. Additionally, the lateral surface in contact with the reference plane of the reference element 13d can be navigated via the reference star 21'.

Accordingly, the present invention can be used to navigate a surface of an instrument. Moreover, due to the unique features of the device, wear of the surface to be navigated and/or to the device itself has a minimal or no effect on the overall navigation accuracy.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A device for determining the position of a plane or recess of an instrument, comprising:
    a positioning element that includes at least one reference point, the spatial position of which can be ascertained by a medical tracking system;
    a position determining element coupled to the positioning element, the position determining element comprising
    at least one reference element that defines a contact plane for contacting a guide surface of the instrument that is subject to wear in use, wherein the at least one reference element has a fixed spacing relative to the at least one reference point,
    at least one pressing element.

2. The device of claim 1, wherein the reference element includes at least one reference plate that lies on the contact plane, the reference plate being insertable into the instrument.

3. The device of claim 2, wherein the pressing element includes at least one pressing plate, wherein the pressing plate is moveable with respect to the at least one reference plate, and at least one component of the movement is substantially perpendicular to the contact plane.

4. The device of claim 3, wherein the pressing plate can be moved onto the contact plane.

5. The device of claim 3, wherein the at least one pressing plate is insertable into the instrument.

6. The device of claim 1, wherein the pressing element is formed as an elastic element or is charged with a force by an elastic element.

7. The device of claim 6, wherein the positioning element can be fixed or arrested by the elastic element.

8. The device of claim 6, wherein a force exerted by the elastic element urges the pressing element toward the reference element.

9. The device of claim 6, wherein a force exerted by the elastic element urges the pressing element away from the reference element.

10. The device of claim 6, wherein the charged force of the elastic element provides a moving force that acts substantially perpendicular to the contact plane.

11. The device of claim 6, wherein the elastic element is a spring.

12. The device of claim 11, wherein the spring is a coil spring or a leaf spring.

13. The device of claim 12, wherein the spring is configured to operate under tension.

14. The device of claim 12, wherein the spring is configured to operate under compression.

15. The device of claim 11, wherein the spring is a torsion spring.

16. The device of claim 1, wherein the instrument is an incision block.

17. The device of claim 1, wherein the positioning element is a reference star and includes at least three markers having a reflective surface.

18. The device of claim 1, wherein the reference element or the pressing element can be rotated about an axis of the positioning element.

19. The device of claim 18, wherein the axis is substantially parallel to the contact plane.

20. The device of claim 18, wherein the axis is substantially perpendicular to the contact plane.

21. The device of claim 1, further comprising a connecting element, the connecting element coupling the positioning element to the position determining element, wherein the connecting element provides for a rotational movement of the positioning element with respect to the position determining element.

22. The device of claim 1, wherein the pressing element and the reference element create an interference fit when both are inserted into the recess of the instrument or an opening of the instrument.

23. The device of claim 1, wherein the pressing element is configured to provide a force perpendicular to the contact plane.

24. A system for positioning an incision block, comprising:
    a device as set forth in claim 1; and
    an incision block.

25. A device for determining the position of a plane or recess of an instrument, comprising:
    a positioning element trackable by a medical tracking system;
    a connector coupled to the positioning element, the connector having a substantially flat plate that defines a reference plane, said reference plane having a fixed spacing relative to the positioning element; and
    a biasing element operatively coupled to the connector, wherein the biasing element provides a force having at least one component that is substantially perpendicular to the reference plane.

26. The device of claim 25, further comprising a connecting element, the connecting element coupling the positioning element to the connector, wherein the connecting element provides for a rotational movement of the positioning element with respect to the connector.

27. The device of claim 25, wherein the biasing element is formed as an elastic element or is charged with a force by an elastic element.

28. The device of claim 27, wherein the elastic element is at least one of a coil spring, a torsion spring and a leaf spring.

29. The device of claim 25, wherein the plate or the biasing element rotatable about an axis of the positioning element.

30. The device of claim 25, wherein the positioning element is a reference star and includes at least three markers having a reflective surface.

31. A system for positioning an incision block, comprising:
    a device as set forth in claim 25; and
    an incision block.

* * * * *